United States Patent [19]

Oscarsson

[11] Patent Number: 4,585,056
[45] Date of Patent: Apr. 29, 1986

[54] HEAT EXCHANGER
[75] Inventor: Rolf A. Oscarsson, Hudson, Ohio
[73] Assignee: Norton Company, Worcester, Mass.
[21] Appl. No.: 601,705
[22] Filed: Apr. 18, 1984
[51] Int. Cl.[4] ............................................. F28F 21/06
[52] U.S. Cl. ...................................... 165/133; 165/142; 165/154; 165/155; 165/905; 422/46
[58] Field of Search ................... 422/46; 128/DIG. 3; 165/46, DIG. 8, 142, 133, 154, 155

[56] References Cited

U.S. PATENT DOCUMENTS

| | | |
|---|---|---|
| Re. 27,100 | 3/1971 | De Wall . |
| 2,374,609 | 4/1945 | McCollum . |
| 2,934,067 | 4/1960 | Calvin . |
| 3,256,883 | 6/1966 | Wall . |
| 3,291,568 | 12/1966 | Sautter . |
| 3,374,066 | 3/1968 | Farrant . |
| 3,468,631 | 9/1969 | Raible et al. . |
| 3,488,158 | 1/1970 | Bentley et al. . |
| 3,502,440 | 3/1970 | Tompkins . |
| 3,615,238 | 10/1971 | Bentley . |
| 3,626,987 | 12/1971 | Bittner ............................ 165/154 |
| 3,729,377 | 4/1973 | Leonard . |
| 3,731,731 | 5/1973 | Kyvsgaard et al. . |
| 3,746,084 | 7/1973 | Ostbo . |
| 3,764,271 | 10/1973 | Brumfield . |
| 3,768,977 | 10/1973 | Brumfield et al. . |
| 3,769,162 | 10/1973 | Brumfield . |
| 3,802,499 | 4/1974 | Garcea . |
| 3,807,958 | 4/1974 | Brumfield et al. . |
| 3,853,479 | 12/1974 | Talonn et al. . |
| 3,870,470 | 3/1975 | Yoshida et al. . |
| 3,892,534 | 7/1975 | Leonard . |
| 3,898,045 | 8/1975 | Bowley . |
| 4,058,369 | 11/1977 | Bentley et al. . |
| 4,065,264 | 12/1977 | Lewin . |
| 4,073,622 | 2/1978 | Luppi . |
| 4,138,288 | 2/1979 | Lewin . |
| 4,138,464 | 2/1979 | Lewin ................................ 422/46 |
| 4,268,476 | 5/1981 | Raible ............................... 422/46 |
| 4,281,981 | 7/1981 | Harnsberger ..................... 422/46 |
| 4,282,180 | 8/1981 | Raible ............................... 422/46 |
| 4,297,318 | 10/1981 | Raible ............................... 422/46 |
| 4,336,224 | 6/1982 | Siposs .............................. 422/46 |
| 4,372,914 | 2/1983 | Raible ............................... 422/46 |
| 4,407,777 | 10/1983 | Wilkinson et al. ............... 422/46 |

FOREIGN PATENT DOCUMENTS

731485  4/1966  Canada ............................... 165/155

Primary Examiner—Albert W. Davis, Jr.
Attorney, Agent, or Firm—Frank S. Chow

[57] ABSTRACT

The present invention relates to a heat exchanger which is specifically adapted for use in connection with blood oxygenators, particularly bubble oxygenators. The core of the heat exchanger is generally cylindrical and closed at both ends. The cylinder is made of thin walled material with good heat exchange properties such as aluminum. The portion of the heat exchanger core which will be exposed to blood is coated with a biocompatible material such as tetrafluoroethylene. The heat exchanger may be connected to a source of heat exchange medium, such as water, through couplings in the top portion of the heat exchanger core. The heat exchange medium is then circulated through the core providing heating or cooling which is capable of heating or cooling blood within a bubble oxygenator. The heat exchanger core is then nested within a suitable receiver. The inner walls of said receiver may be reticulated in order to facilitate exchange of heat between the heat exchanger core and a fluid, such as blood, flowing between the outer wall of the heat exchanger core and the inner wall of the shell.

8 Claims, 6 Drawing Figures

HEAT EXCHANGER

BACKGROUND

1. The Field of the Invention

The present invention relates to a heat exchanger for use in regulating the temperature of blood flowing in an extracorporeal circuit, such as through a bubble blood oxygenator.

2. The Prior Art

Many types of heart surgery require the use of an extracorporeal cardiopulmonary bypass circuit while the surgery is being performed. The role of such a circuit is essentially to take over the function of the heart and lungs while the surgical procedure is performed. This type of circuit is used to oxygenate and pump blood, just as the heart and lungs normally oxygenate and pump blood.

The basic components of such extracorporeal bypass circuits are, as would be expected, a pump which forces the blood through the circuit and back into the patient's body and an oxygenator which adds oxygen to the blood while providing for the removal of carbon dioxide. The most commonly used process for oxygenation of blood involves mixing small bubbles of oxygen rich gas with the blood in such a manner that the oxygen can be absorbed by the blood. Although many different types of "bubble oxygenators" have been developed, typically bubble oxygenators consist of an oxygenating section, a defoaming section and an arterial reservoir.

Oxygen and other gases are introduced into the oxygenating section through small tubes or a porous member. Each small tube or porous member creates small bubbles which are dispersed in the blood. As the gases and blood are mixed together, oxygen is absorbed by the blood and carbon dioxide is liberated. In most devices, the majority of the oxygenation takes place in this section. However, in some devices the blood has a short residence time in the oxygenating section; thus, oxygenation continues to occur as the blood passes through the subsequent defoaming section.

As oxygen is bubbled through the blood in a bubble oxygenator, a certain amount of foaming necessarily occurs. This foam, and any entrapped air bubbles, must be removed from the blood before it is reinjected into the patient; otherwise, the entrapped air bubbles can form an ambolus which can do sever damage to the patient. Defoaming is generally accomplished by passing the blood over a material having a large surface area which has been treated with a defoaming agent.

The blood next flows into the arterial reservoir. The arterial reservoir provides an area where the defoamed blood is collected before reinjection into the patient. The reservoir acts as a safety feature in helping avoid accidental pumping of air into the blood lines. Should the blood supply to the oxygenator be accidently stopped, the reservoir must contain sufficient blood to allow the perfusionist to stop the output from the oxygenator before air enters the arterial line.

During heart surgery while blood is flowing through the extracorporeal circuit, including the oxygenator, it becomes critical to have the capability of controlling the temperature of the blood. As would be expected, blood flowing outside the body for a significant period of time will tend to cool to room temperature. This cooling of the blood may or may not be desirable at any particular point in the surgery, however, it is clear that when the surgery is being completed it is desirable to warm the blood to normal body temperature in order to bring the patient back to normal temperature.

In addition, it is now common practice to use hypothermia during heart surgery. Reducing body temperature can significantly reduce the demand for oxygen by various vital organs. Specifically, the literature indicates that a patient's oxygen demand is decreased to about one-half at 30° C., one-third at 25° C., and one-fifth at 20° C. Hypothermia is particularly useful in protecting organs such as the kidneys, heart, brain and liver which have a high demand for oxygen and require a high degree of perfusion. Mild (37°–32° C.), moderate (32°–28° C.), deep (28°–18° C.), and profound (18°–0° C.) hypothermia have all been employed. It has been found that moderate hypothermia is usually sufficient in a routine open-heart case. However, deep and profound hypothermia are sometimes advocated, particularly in cases of surgical repair of congenital defects in infants and small children.

One of the primary concerns in the use of hypothermia is the time which it takes to cool and reheat the blood. The time it takes to change the blood temperature is time added onto the length of the surgical procedure. If this time is minimized there is more time to perform the open-heart procedure and the total time taken to perform the operation is minimized. It is clear that reducing these time periods reduces the general trauma suffered by the patient. As a result, it is important that the heat exchanger be as efficient as possible in changing blood temperature.

It can be seen, therefore, that a means for controlling blood temperature in the extracorporeal circuit becomes critical, particularly when hypothermia is employed. Various types of heat exchanging devices have been used in order to attempt to regulate blood temperature during heart surgery.

Many early heat exchangers were placed in the extracorporeal circuit in addition to the oxygenator, rather then being incorporated within the oxygenator itself. In other words, the heat exchanger was a third major element in the circuit. The resulting circuit was comprised of a pumping mechanism, an oxygenator and a heat exchanger. The heat exchanger could take a variety of forms. Typical heat exchangers employed hollow coils or plates through which a heat exchange medium was circulated. The heat exchange medium was typically tap water, readily available in the operating room.

Subsequently, the heat exchanger and the oxygenator were attached within a single structure, typically made of molded plastic. The design of the oxygenator and the heat exchanger remained essentially the same. Blood would first flow through the oxygenator and, when completely oxygenated, would flow into the heat exchanger. However, linking the two elements within a single structure eliminated some problems previously encountered. Various segments of tubing could be eliminated and the oxygenator and heat exchanger were positioned so that the blood could readily travel through both without constant concern about positioning the various parts of the circuit.

Later devices incorporated the heat exchanger and the blood oxygenator into a unitary device. In these devices it was the general practice to have the blood mix with oxygen in the oxygenating section and then travel into a heat exchanger section. Following the heat exchanger section, the blood would flow through the defoaming section and in to the arterial reservoir for reinjection into the patient. The heat exchange function and the oxygenating function were thus combined into a single device. However, the heat exchanger, even though incorporated into the oxygenator, was still of the same general type used before.

Examples of this type of oxygenator-heat exchanger configuration include the Harvey and Shiley oxygenators. The Harvey oxygenator is a disposable, hardshell, concentric, bubble oxygenator. See, Brumfield, "A Bubble Oxygenator and Heat Exchanger," U.S. Pat. No. 3,768,977 (Issued Oct. 23, 1973). The oxygenator is hung with a mounting bracket which holds the oxygenator at the top and bottom. Venous return and cardiotomy drainage, as well as gas, flows to the bottom of the oxygenator. The oxygen disperser is a sintered plate which produces bubbles of various sizes. The oxygenated blood travels upward through a series of parallel vertical tubes. An integral heat exchanger surrounds the tubes and is in contact with the blood path through the oxygenating as well as defoaming area, and in the arterial reservoir.

The Shiley oxygenator uses the same basic elements but employs a different heat exchanger. See, Lewin, "Blood Oxygenator with Integral Exchanger For Regulating the Temperature of Blood in an Extracorporeal Circuit," U.S. Pat. No. 4,065,264 (Issued Dec. 27, 1977). In the Shiley device the heat exchange medium travels through a coil. The blood reaches the coil, as in the Harvey device, after oxygenation but before defoaming. Positioned on the outside of the Shiley heat exchanger coil is a continuous hollow helical rib. The rib is employed in order to achieve more efficient heat exchange through increasing the residence time of the blood while traveling past the heat exchanger.

Other devices incorporate variations of the Shiley or Harvey concepts. For example, dual coils of the same general type use in the Shiley device have been used. In addition, several different configurations of the Harvey concept have been used including a series of parallel tubes running the length of the oxygenator. However, in order to obtain adequate heat exchange most prior devices employ convoluted and tortuous blood flow paths in order to increase heat exchange by attempting to increase blood residence time and decrease the boundary layer effect. However, none of the prior devices were able to provide adequate heat exchange without unduly increasing the surface area exposed to the blood, which in turn increases damage to the blood including hemolysis.

Pierre M. Galletti in the book *Heart*-Lung Bypass identified several criteria for an acceptable heat exchanger. The criteria are as follows:

(1) The material used in the heat exchanger should be non-toxic. It is clear that a material which leaches into the blood would be unacceptable. As a result many prior art devices have used stainless steel heat exchangers. While essentially non-toxic, stainless steel is not particularly blood compatible.

(2) The heat exchanger should be either easy to clean or disposable. It can be readily seen that devices using intricate flow paths including complex coil configurations could be extremely difficult to clean.

(3) There must be no internal leakage. If water or other heat exchange medium were allowed to leak into the blood, it is clear that the impact to the patient could be devastating.

(4) The heat exchanger should not significantly increase the blood flow resistance. It will be appreciated that the convoluted flow paths created in prior devices could not help but greatly increase flow resistance.

(5) The heat exchanger should cause a minimum of trauma to the blood. Again, the more involved the flow path and the tubing becomes, the more potential there is for trauma to the blood. In addition, exposing the blood to stainless steel is likely to cause more blood trauma than exposing the blood to more biocompatible surfaces such as various plastics.

(6) The heat exchanger must be efficient. Included within this criteria are the considerations of maximizing heat exchanged while minimizing surface area exposed and minimizing the volume of blood necessary to prime the oxygenator-heat exchanger.

(7) Finally, the heat exchanger must be reasonably inexpensive. No prior device fully accomplished the objects identified by Galletti.

Accordingly, what is needed in the art is a heat exchanger for use in connection with a bubble blood oxygenator which fulfills more closely the Galletti criteria. Particularly, what is needed is an efficient heat exchanger which does not employ a convoluted or tortuous flow path and which only exposes the blood to a biocompatible surface. It would be a further advancement in the art to provide a heat exchanger which is simple to construct and operate and which is easy and inexpensive to manufacture. Particularly, the heat exchanger should be easily incorporated into a standard bubble oxygenator. Such a device is disclosed and claimed herein.

OBJECTS AND BRIEF SUMMARY OF THE INVENTION

In the presently preferred embodiment the heat exchanger is generally cylindrical in shape. The heat exchanger core is completely enclosed with the exception of two couplings in the top of the device for introducing a heat exchange medium into the heat exchanger core and then transporting the heat exchange medium back out of the core. Heat exchange medium flows into the core and is transported through an internal tube to the bottom of the core and then flows upwardly either heating or cooling, as the case may be, the outer walls of the heat exchanger core. Finally, the heat exchange medium again flows out of the core through an outlet coupling in the top.

While the heat exchanger could be used separately, it is presently anticipated that the heat exchanger will be positioned within a conventional bubble oxygenator. The heat exchanger will be placed within the oxygenator between the oxygenating section and the defoaming section.

The geometry of the heat exchange surface of this invention will expose much less surface area to the blood than the prior art devices, particularly those devices employing coil-type heat exchangers. Heat transfer efficiency of the device is uniquely increased so that the benefits of simplified construction and assembly can be achieved. The heat exchanger core as presently designed will minimize trauma to the blood because the blood will be allowed to flow in a direct path upward along smooth outer walls of the heat exchanger core. The heat exchange surface is not interrupted by irregular surfaces which are expensive to manufacture and which tend to traumatize blood cells. When desired, the heat exchanger core may be inserted into a mating plastic receiver which is configured to disturb the boundary layer effect in flowing blood and direct the blood into contact with the smooth surface of the heat exchanger core.

The general object of the present invention is to provide significant improvements over the prior art in the areas identified by Galletti.

Accordingly, it is an object of the present invention to provide a heat exchanger for use in connection with a bubble oxygenator which can be easily incorporated and housed within the oxygenator.

A further object of the invention is to provide a heat exchanger which is effective in transferring heat while at the same time exposes only a small amount of surface area to the blood and also requires a low priming volume.

A related object of the invention is to provide a heat exchanger which is capable of quickly cooling or warming blood in order to minimize the time required for surgery.

Another object of the invention is to provide a heat exchanger which minimizes the trauma inflicted on the blood.

An additional object of the invention is to provide a heat exchanger which is simple to construct and operate and which is easy and inexpensive to manufacture.

Other objects and advantages of the invention will become more fully apparent from the following detailed description and appended claims, taken in conjunction with the accompanying drawings.

DETAILED DESCRIPTION OF THE PREFERRED EMBODIMENTS

Figure 1:
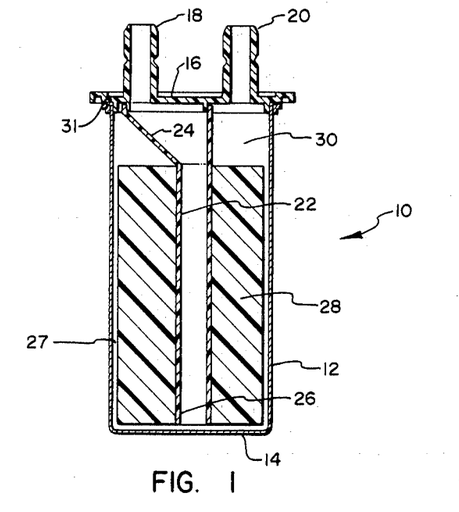
FIG. 1 is a longitudinal cross-sectional view of the presently preferred embodiment of the heat exchanger core.

The present invention can best be understood by reference to the drawings wherein like parts are designated with the numerals throughout. FIG. 1 is a cross-sectional view of a presently preferred embodiment of the present invention. The heat exchanger core, generally designated 10, is constructed in a generally cylindrical shape (see also FIG. 3). In a presently preferred embodiment the outer walls 12 as well as the base 14 of the heat exchanger core 10 are constructed of a relatively thin layer of aluminum. It is anticipated that the aluminum structure would then be coated with a thin layer of biocompatible material. Any type of biocompatible material could be used including polyurethanes or other similar polymers; however, it is presently anticipated that the structure will be coated with a polymer of tetrafluoroethylene. As a result, the outside surfaces of the heat exchanger core 10 would be readily usable in communication with blood in a bubble oxygenator.

The heat exchanger core 10 may also have a top portion 16. This top portion may be constructed as part of the heat exchanger core 10 or it may comprise a reusable detachable lid. In either case the function of top portion 16 is the same in that it seals the heat exchanger core and acts as a support structure for any desired couplings needed in order to operate the heat exchanger.

In the presently preferred embodiment of the invention as illustrated in FIG. 1, two heat exchanger couplings are positioned in top portion 16. The purpose of the couplings is to allow a heat exchange medium to be introduced into the device and to be subsequently discharged once it has flowed through the device. Coupling 18 is an inlet coupling and coupling 20 is an outlet coupling. Both couplings can be standard couplings commonly used to attach tubing of the desired diameter.

Positioned within the heat exchanger is tube 22. Tube 22 has an enlarged funnel 24 which communicates with inlet coupling 18 and with the interior of the tube 22. The bottom end 26 of tube 22 is open to the base 14. The function of tube 22 is to transport a heat exchange medium which is introduced through inlet coupling 18 to the bottom of the heat exchanger core 10.

Plug 28 is positioned within heat exchanger core 10 so as to occupy the center portion of the heat exchanger 10 leaving space for the heat exchange medium to flow around plug 28 and against the walls 12 as efficiently as possible. Thus, a smaller volume of heat exchange medium is required to maintain temperature of the surface of walls 12 and base 14.

Typically, a length of tubing carrying water or other heat exchange medium of the desired temperature will be attached to inlet coupling 18. The heat exchange medium then flows into the heat exchanger and down through tube 22. The heat exchange medium then travels out of the base of nozzle tube 22 and beneath plug 28. When the medium reaches the bottom edge of the heat exchanger wall 12, it travels upwardly moving in the space 27 between plug 28 and heat exchanger wall 12. As the medium travels along the heat exchanger wall 12 and the base 14 of the heat exchanger core 10, it proceeds to heat or cool the core 10.

Once the heat exchange medium reaches the top of plug 28 it is collected in the core's upper reservoir 30 and then is discharged through outlet coupling 20. The heat exchange medium may be disposed of or recirculated according to known technology.

The heat exchanger core 10 is a very simple apparatus to construct. It does not employ a complex network of coils or tubes nor does it require extensive structures to be attached to its outer surface as do prior devices. As a result the heat exchanger is simple and easy to manufacturer. The heat exchanger core 10 can also be manufactured at a very low cost and is, therefore, readily disposable. In addition, because of the simple cylindrical structure of the heat exchanger core 10, the device could easily be sterilized if necessary. Thus, the heat exchanger core 10 fully satisfies the requirement that a heat exchanger be easy to clean and sterilize or be disposable.

Because of the simple basic structure of the heat exchanger core 10, the device is safe in operation. There is no complex series of seams or connections which occasionally caused leakage in prior art devices. The only connection internal to the heat exchanger core is at the junction 31 of the wall 12 and the top 16. Junction 31 is bonded fluid-tight and is easily tested for integrity. As a result, the heat exchanger satisfies the requirement that a heat exchanger have structural integrity and not leak.

The heat exchanger core 10 is complemented by a receiver 52 into which the core 10 is inserted. While the core receiver 52 may be a separate container, in the illustrated embodiment the receiver 52 forms part of a bubble oxygenator 50. One suitable type of bubble oxygenator usable with the present invention is disclosed in copending application Ser. No. 541,988, filed Oct. 14, 1983, which is incorporated herein by reference.

Figure 2:
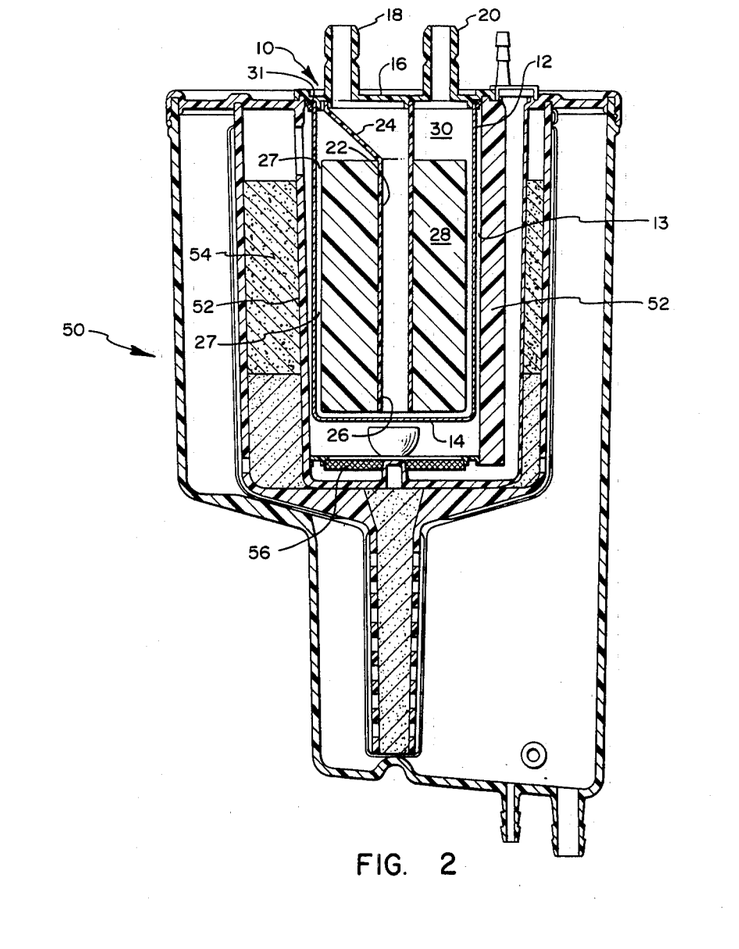
FIG. 2 is a longitudinal cross-sectional view of the heat exchanger positioned within a bubble oxygenator.

FIG. 2 is a cross-sectional illustration of the heat exchanger core 10 positioned within the bubble oxygenator 50. The heat exchanger core 10 is nested within the receiver 52 such that a compartment is formed by the receiver 52 and the defoaming section 54 of the oxygenator 50 and has as its base a sparger plate 56 which is used to introduce oxygen into the blood.

Blood and oxygen, bubbled through the sparger plate 56, are mixed in the area beneath the base 14 of the heat exchanger core 10. The oxygenated blood then travels upward through the space formed by the walls 12 of the heat exchanger core 10 and the walls 52 of the defoaming section 54 of the oxygenator 50. Space 13 is intentionally limited to a small dimension which is a function of the flow rate of blood across the heat exchanger. In the illustrated embodiment, the space 13 has a dimension between 0.120 inches (3.05 mm) and 0.040 inches (1.02 mm). As the blood travels in space 13 along the walls 12 of the heat exchanger core 10 heat is transferred between the blood and the heat exchanger core 10.

Several characteristics involving the structure and use of the heat exchanger core 10 are unique and are illustrated in FIG. 2. First, it will be readily appreciated that when using the present invention the volume of blood necessary to prime the oxygenator 50 is very significantly reduced. The vast majority of the volume within the compartment formed by the walls of the receiver 52 and the sparger plate 56 is filled by the heat exchanger core 10. This is in contrast to prior art devices such as those employing coils. In those devices the coils occupied much less volume and the difference in volume had to be compensated for by adding additional blood to the system. For example, the volume of blood required to prime a typical oxygenator employing a coil heat exchanger or a tube heat exchanger is approximately 335 cc and 289 cc respectively. This is in contrast to approximately 27 cc required to prime the present invention. As discussed above, it is important to minimize the volume of blood required for priming in order to minimize the problems encountered in obtaining and introducing into a patient transfusion blood.

An additional significant improvement found in this device is the straight and unobstructed blood flow path created by the straight walls 12 of the heat exchanger core 10. In previous oxygenators, particularly those using coiled heat exchangers, the blood flow path was convoluted and often tortuous. Some coil devices made the blood flow path even more tortuous by including ribbing or other irregularities on the outer walls of the heat exchanger coils. While this was done specifically in order to minimize the boundary layer effect by breaking up the flow path, it makes fabrication of the heat exchanger complex and expensive.

Figure 4:
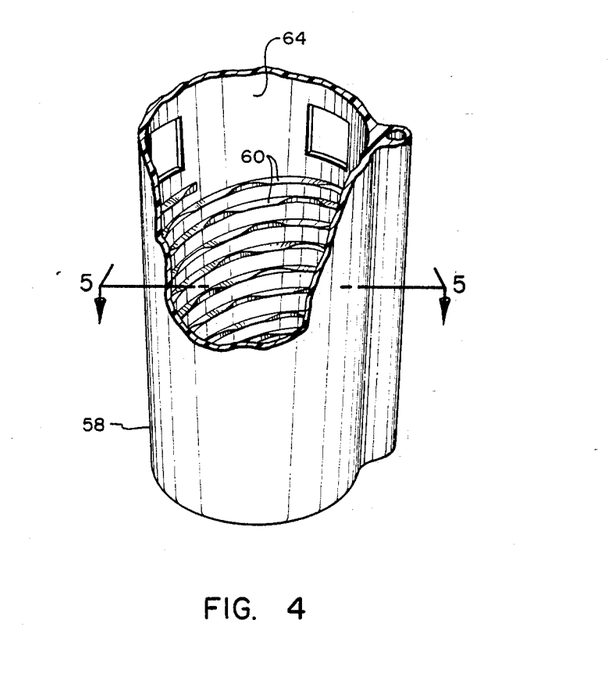
FIG. 4 is a cut-away perspective view of one embodiment of a heat exchanger shell.
Figure 5:
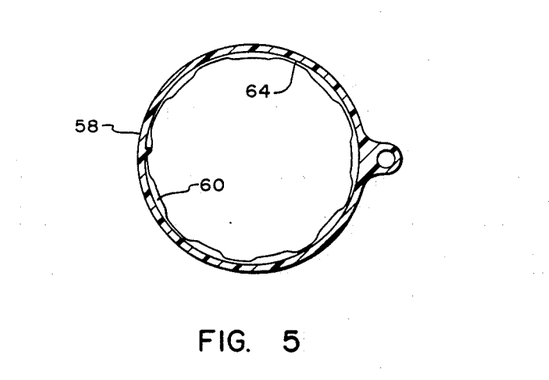
FIG. 5 is a horizontal cross-sectional view of the heat exchanger shell as indicated by line 5—5 in FIG. 4.

FIG. 4 is a cut-away perspective view of another preferred embodiment of a heat exchanger receiver 58 and FIG. 5 is a cross-sectional view of the receiver 58 along line 5—5 as shown in FIG. 4. The receiver 58 could be an integral part of the bubble oxygenator 50 or it could be a separate component manufactured from polycarbonate or other suitable moldable material. In this embodiment, the interior of the receiver 58 is reticulated to present a series of integrally molded baffles 60. The baffles 60 may have any one of a variety of configurations and are preferably molded as part of the interior surface of receiver 58. The baffles 60 are illustrated as having a generally helical pattern in order to enable the shell to be easily removed from a mold. In the present device the baffles 60 can be included on the inexpensive plastic shell rather than, as in previous devices, on the expensive metal heat exchanger core. Other types of baffles are of course possible. Such baffles could include any structure which would tend to induce turbulent flow.

The function of baffles 60 is to reduce the tendency for formation of a fluid boundary layer on either the inner wall 64 of the shell 58 or the outer wall 12 of heat exchanger core 10 and to induce turbulent flow.

When baffles 60 are incorporated into the inner walls 64 of the receiver 58, it is found that heat exchange takes place more efficiently. As would be expected, the baffles 60 disrupt the flow of fluid through the device causing turbulence which breaks up the boundary layer of fluid. This facilitates a more complete exchange of heat between the heat exchanger core 10 and the blood or other fluid being transported through the device.

As will be discussed more fully below, even without baffles 60, the heat exchanger is reasonably effective in the transfer of heat and has a high transfer coefficient. The use of baffles 60 merely increases the effectiveness of the device and increases further the heat transfer coefficient.

The present device is very efficient in the exchange of heat, allowing the device to minimize the surface area in contact with the blood. For example, typical tube and coil heat exchangers have approximately 2,378 cm$^2$ and 1,578 cm$^2$ respectively of heat transfer surface area in contact with the blood. The present invention, on the other hand, has only approximately 263 cm$^2$ of surface area in contact with the blood. Yet, heat transferred by the various devices is very comparable. Indeed, the overall heat transfer coefficient of the present device expressed in calories/cm$^2$ minute °C. is several times that of the coil and tube devices. Table 1 summarizes the heat transfer efficiencies of the present invention compared with typical coil and tube devices.

TABLE 1

|  | FIG. 2 Embodiment | FIG. 4 Embodiment | Typical Tube Heat Exchanger | Typical Coil Heat Exchanger |
|---|---|---|---|---|
| 1. Available Heat Transfer Surface Area, Blood Side (cm$^2$) | 263 | 263 | 2,378 | 1,758 |
| 2. Blood side void volume, or priming volume (cm$^3$) | 27 | 27 | 289 | 335 |

TABLE 1-continued

|  | | FIG. 2 Embodiment | FIG. 4 Embodiment | Typical Tube Heat Exchanger | Typical Coil Heat Exchanger |
|---|---|---|---|---|---|
| 3. | Ratio of Surface area to Priming volume ($cm^2/cm^3$) | 9.6 | 9.6 | 8.2 | 5.2 |
| 4. | Heat exchanger wall thickness (cm) | 0.02 | 0.02 | 0.04 | 0.06 |
| 5. | Reynolds Number | 978 | 978 | 307 | 434 |
| 6. | Time required to reduce reservoir temperature from 38° C. to 26° C. (min.) | 4.22 | 3.33 | 3.43 | 2.35 |
| 7. | Overall heat transfer coefficient (cal/$cm^2$, min. °C.) | 4.62 | 6.37 | 0.67 | 1.66 |
| 8. | Heat Transferred - (cal/min) | 25,735 | 32,546 | 31,789 | 46.170 |

All calculations are based on the average value of three separate runs for each heat exchanger. Conditions common to all tests are:
1. Air input into sparger plate - 2¼ psig.
2. Coolant flow rate - 5.76 1/min @ 9° C.
3. Media flow rate - 2.61 1/min @ 38° C.
4. Media reservoir - 7000 ml.

From the above Table it can be seen that the present simple and inexpensive heat exchanger is approximately as effective as other complicated and expensive heat exchangers. Indeed the overall heat transfer coefficient of the present device, whether or not it employs baffles, is several times that of typical coil and tube devices.

Figure 6:
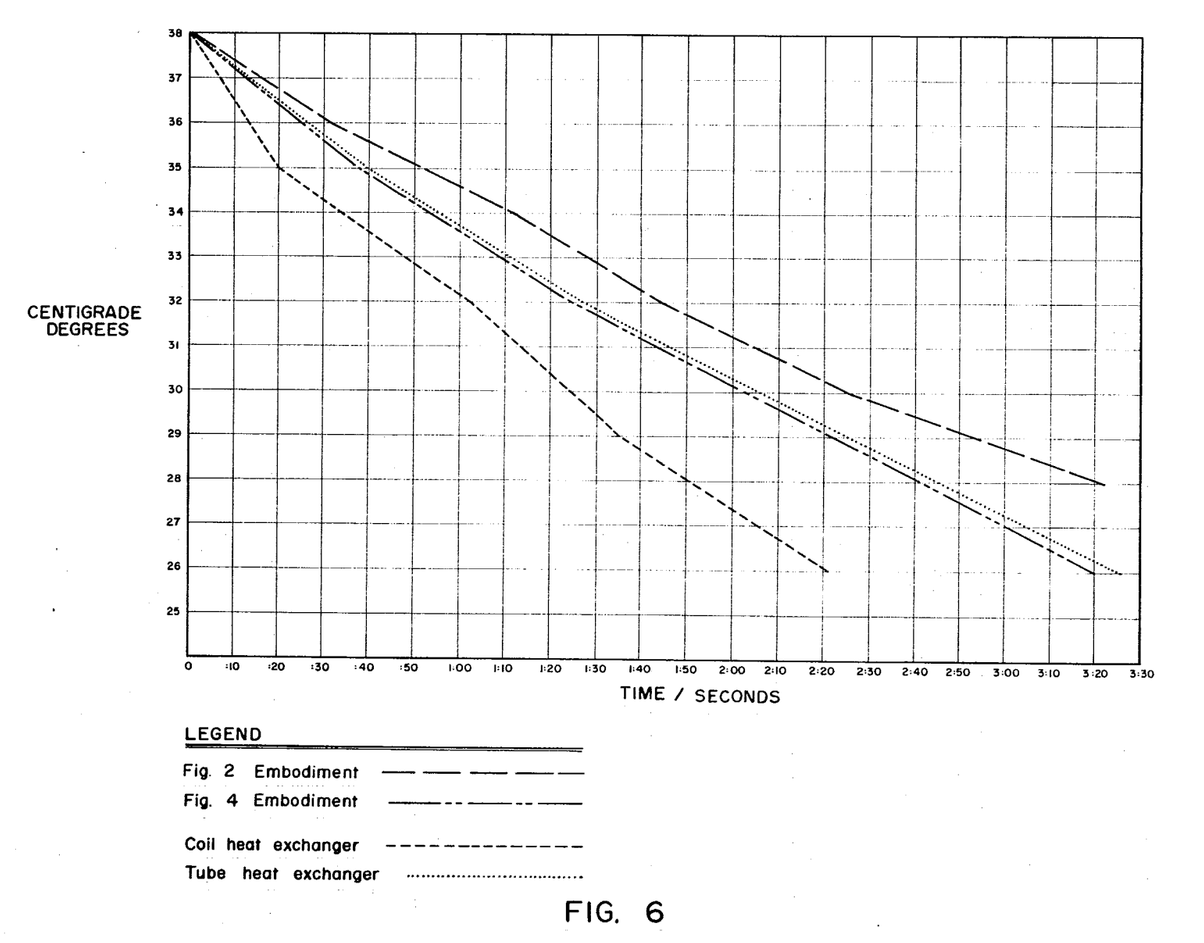
FIG. 6 is a time-temperature graph illustrating the time various heat exchangers take to cool a volume of liquid from 38° C. to approximately 28° C.

A further illustration of the effectiveness of the present invention is shown in FIG. 6. FIG. 6 is a graphical representation of a time-temperature heat exchange curve. The vertical axis shows temperature in degrees centigrade and the horizontal axis shows time. The conditions under which the illustrated tests run were the same as those described above in Table 1. The devices tested included a typical coil heat exchanger, a typical tube heat exchanger and the present invention with and without baffles. As can be seen, the two embodiments of the present invention approximate the effectiveness of the conventional devices. Furthermore, this is accomplished in a simple inexpensive device which requires less than one-tenth the priming volume required by the other devices and has less than 15% of the available heat transfer surface area of the other devices.

Figure 3:
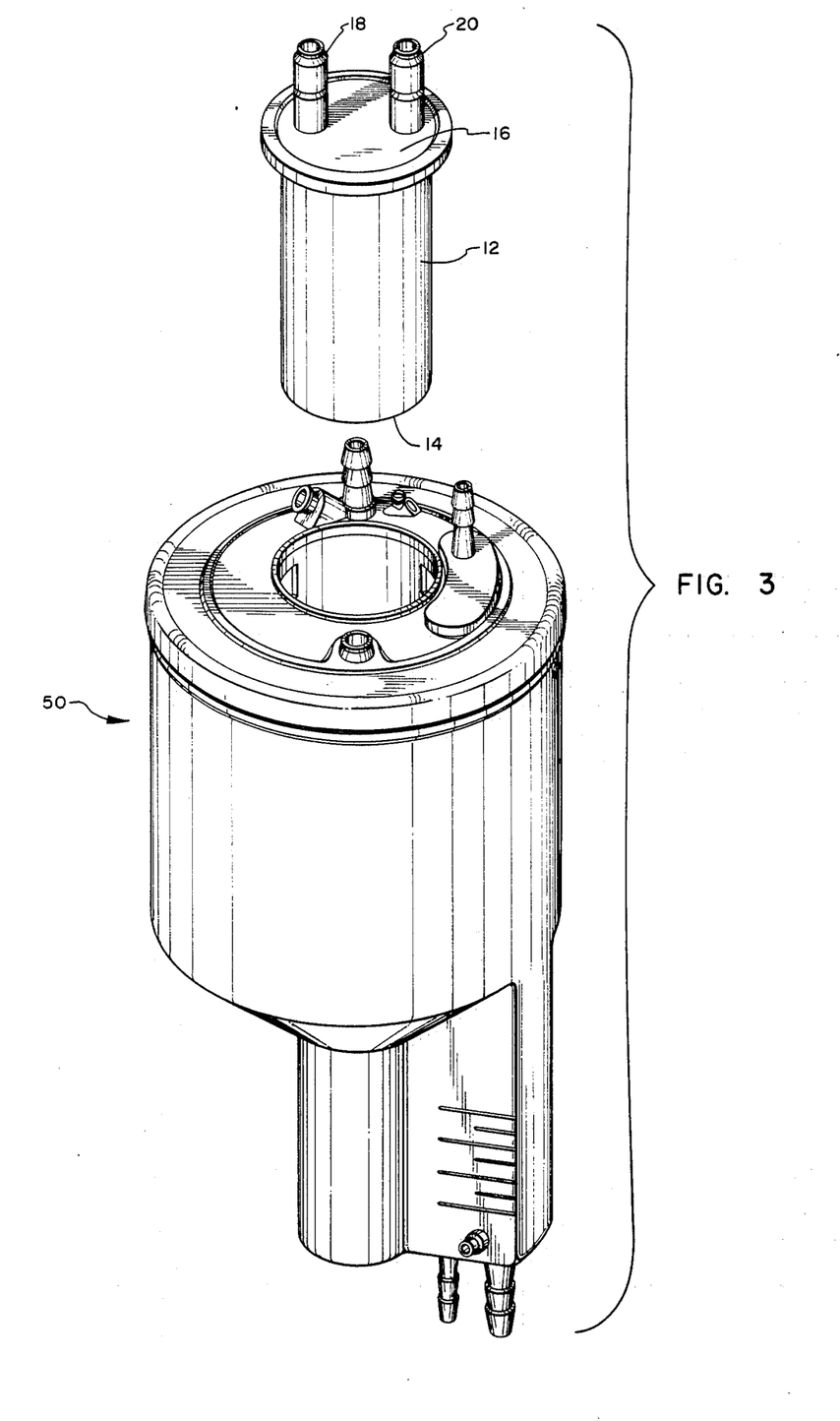
FIG. 3 is an exploded perspective view of the heat exchanger core as well as the bubble oxygenator illustrated in FIG. 2.

The heat exchanger is also adaptable for use in a wide variety of situations. As is illustrated in FIG. 3, the heat exchanger core 10 can easily slide into a conventional blood oxygenator. Modifications in the size of the heat exchanger may be required for use in particular oxygenators, however, no significant change in design will be required. In addition, the heat exchanger could easily be used for heating and cooling in environments other than blood oxygenators. As a result, the present invention meets the final requirement of an acceptable heat exchanger in that it is flexible and adaptable for use in a variety of situations.

In summary, the present device represent a significant improvement over the prior art in meeting the various criteria of an ideal heat exchanger. The heat exchanger is non-toxic in that all surfaces exposed to the blood are coated with a biocompatible material. The heat exchanger is, because of its shape, easy to clean and sterilize. However, because of the low cost of manufacture it would be expected that the heat exchanger will be disposed of after use. The device is not likely to leak because there are no connections or joints within the blood chamber. The device will not significantly increase the resistance to flow because the flow path is straight and unobstructed. Trauma to the blood will also be minimized because of the use of a biocompatible coating and because of the direct blood flow path. The device is efficient in the transfer of heat while at the same time exposing the blood to a small surface area. The device also requires a priming volume of only about one-tenth of the priming volume required in typical prior devices. Finally, the device is adaptable for use with a wide variety of bubble oxygenators and also for possible use apart from bubble oxygenators.

The invention may be embodied in other specific forms without departing from its spirit or essential characteristics. The described embodiment is thus to be considered in all respects only as illustrative and not restrictive. The scope of the invention is, therefore, indicated by the appended claims rather than by the foregoing description. All modifications or changes which come within the meaning and range of equivalency of the claims are to be embraced within their scope.

What is claimed and desired to be secured by United States Letters Patent is:

1. A heat exchanger for use in controlling temperature of blood in an extracorporeal blood circuit comprising:

an enclosed cylindrical heat exchange core having a top portion and relatively straight non-convoluted outer cylindrical and bottom walls with a smooth outer heat exchange surface coated with a polymer of tetrafluoroethylene, of relatively small blood compatible surface area and low resistance to blood flow and a plug positioned within said core such that there is a relatively small space between the plug and said outer cylindrical and bottom walls;

means for circulating a relatively small volume of heat exchange medium through the relatively small space and in contact with the bottom wall, then upwardly against the outer cylindrical wall and out of said core;

a receiver including an inner wall forming a compartment of specific volume about and into which the core can be nested so that the coated outer smooth heat exchange surface of the core is narrowly spaced at a predetermined small distance of from 0.040 inches (1.02 mm) to 0.120 inches (3.05 mm) from the inner wall of the receiver and the core fills a majority of the specific volume of the compartment; and means for directing blood into and upwardly through an unobstructed narrow space between the coated outer smooth heat exchange surface of the core and the inner walls of the receiver whereby the blood flows unobstructed in a narrow stream over a compatible, smooth, low resistance, easily cleaned and sterilized non-toxic highly efficient relatively small heat exchange surface area of the core requiring much less blood to prime and a small volume of heat exchange medium flow.

2. A heat exchanger as defined in claim 1 further comprising an inlet coupling and an outlet coupling attached to the top portion of the core for placing said core in communication with a source of heat exchange medium.

3. A heat exchanger as defined in claim 2 further comprising a tube positioned within said core and in communication with the inlet coupling at one end and the bottom of the core at its other end.

4. A heat exchanger as defined in claim 1 wherein the core is made of aluminum.

5. A heat exchanger as defined in claim 1 wherein the top portion of the core is a removable lid.

6. A heat exchanger as defined in claim 1 wherein the receiver is made of a plastic material.

7. A heat exchanger as defined in claim 1 wherein the inner walls of the receiver are smooth.

8. A heat exchanger as defined in claim 1 wherein the inner walls of the receiver are reticulated.

* * * * *